(12) United States Patent
Hertwig et al.

(10) Patent No.: US 9,956,330 B2
(45) Date of Patent: May 1, 2018

(54) MEDICAL DRAINAGE TUBE

(71) Applicant: ASSKEA GMBH, Gebesee (DE)

(72) Inventors: Sven Hertwig, Grueningen (DE); Marco Graf, Obernissa (DE)

(73) Assignee: ASSKEA GMBH, Gebesee (DE)

(*) Notice: Subject to any disclaimer, the term of this patent is extended or adjusted under 35 U.S.C. 154(b) by 587 days.

(21) Appl. No.: 14/425,632

(22) PCT Filed: Aug. 15, 2013

(86) PCT No.: PCT/DE2013/100295
§ 371 (c)(1),
(2) Date: Jun. 25, 2015

(87) PCT Pub. No.: WO2014/036993
PCT Pub. Date: Mar. 13, 2014

(65) Prior Publication Data
US 2015/0290367 A1    Oct. 15, 2015

(30) Foreign Application Priority Data
Sep. 5, 2012    (DE) .................. 10 2012 108 248

(51) Int. Cl.
*A61M 1/00*    (2006.01)
*A61M 27/00*    (2006.01)
*A61M 25/00*    (2006.01)

(52) U.S. Cl.
CPC .......... *A61M 1/0092* (2014.02); *A61M 1/008* (2013.01); *A61M 1/0031* (2013.01); *A61M 1/0086* (2014.02); *A61M 1/0088* (2013.01); *A61M 25/0029* (2013.01); *A61M 27/00* (2013.01); *A61M 2205/7518* (2013.01)

(58) Field of Classification Search
CPC .............. A61M 1/0092; A61M 1/0086; A61M 1/0031; A61M 1/008; A61M 1/0088; A61M 25/0029; A61M 27/00; A61M 2205/7518
See application file for complete search history.

(56) References Cited

U.S. PATENT DOCUMENTS

| 4,508,533 A | 4/1985 | Abramson |
| 4,735,606 A * | 4/1988 | Davison .............. A61M 1/0058 604/118 |

(Continued)

*Primary Examiner* — Leslie Deak
*Assistant Examiner* — Gabriella Burnette
(74) *Attorney, Agent, or Firm* — Norman B. Thot

(57) ABSTRACT

A medical drainage tube for treating wounds with negative pressure includes a suction tube, a suction connector, and a ventilation sleeve. The suction tube includes a suction lumen, and a ventilation lumen including a lumen outer wall and an opening. The ventilation sleeve is arranged at the opening to surround the suction tube. The ventilation sleeve includes a sleeve wall including a sleeve inner wall arranged towards the suction tube, an annular groove arranged in the sleeve inner wall, a filter compartment arranged in the sleeve wall, a bacterial filter arranged in the filter compartment, and an air inlet arranged in the filter compartment. The annular groove communicates with the opening. The bacterial filter communicates with the annular groove. The air inlet connects the bacterial filter with the atmosphere. A part of the ventilation lumen between the annular groove and a proximal end of the suction tube is sealed off.

4 Claims, 3 Drawing Sheets

(56) References Cited

U.S. PATENT DOCUMENTS

| | | |
|---|---|---|
| 5,738,656 A | 4/1998 | Wagner |
| 2007/0167927 A1 | 7/2007 | Hunt et al. |
| 2010/0145289 A1 | 6/2010 | Lina et al. |
| 2010/0262095 A1 | 10/2010 | Hall |

* cited by examiner

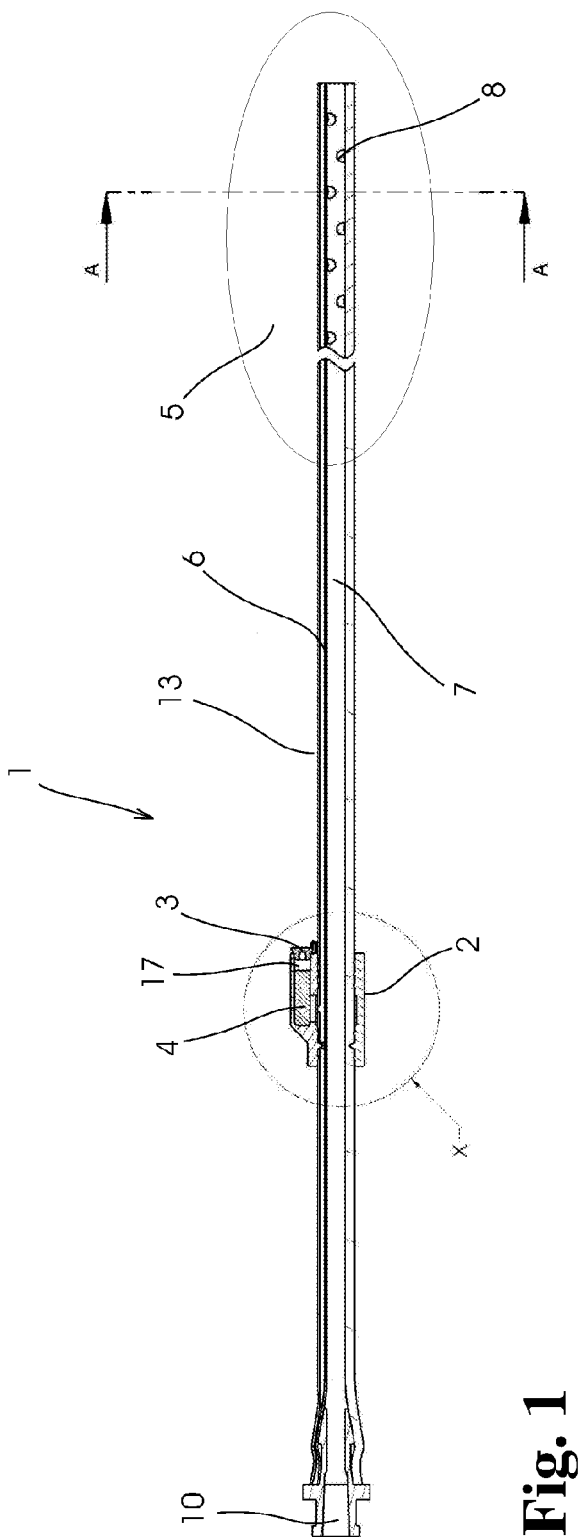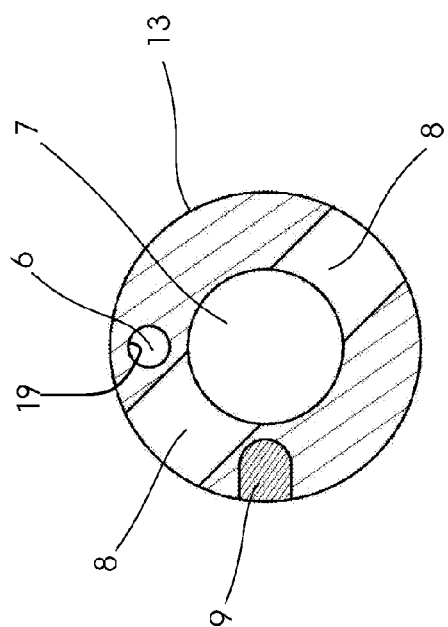

MEDICAL DRAINAGE TUBE

CROSS REFERENCE TO PRIOR APPLICATIONS

This application is a U.S. National Phase application under 35 U.S.C. § 371 of International Application No. PCT/DE2013/100295, filed on Aug. 15, 2013 and which claims benefit to German Patent Application No. 10 2012 108 248.0, filed on Sep. 5, 2012. The International Application was published in German on Mar. 13, 2014 as WO 2014/036993 A1 under PCT Article 21(2).

FIELD

The present invention relates to a medical drainage tube for the treatment of wounds using a negative pressure generated by a medical suction apparatus.

BACKGROUND

In order to promote the healing process of open wounds, in addition to the usual suctioning of wound secretions, it is known to continuously or intermittently subject the wound to a defined negative pressure. The migration of the epithelial tissue and the subcutaneous tissue surrounding the wound toward the wound is thereby increased and a faster wound closure is achieved.

The wound to be treated must thereby be sealingly closed by suturing or stapling so that a negative pressure can be built up on the wound by installing a suction tube. If it is not possible to seal off the wound from atmospheric pressure, for example, in the case of extensive wounds, the wound is sealed off by covering it with adhesive bandages or wound dressings.

In order to discharge the accumulation of secretions occurring during the natural healing process and during a supportive negative pressure treatment, a drainage tube is commonly placed into the wound and connected to a medical suction device with a secretion receptacle. Such a wound treatment device has previously been described, for example, in EP 0 853 950 B1 In which a special wound dressing pad. In order to discharge extract secretions from a wound into a secretion receptacle, a certain pressure differential between the pressure in the wound cavity and the atmospheric pressure, i.e., a certain ventilation of the wound cavity, must be provided. For example, germs in the surrounding air must not enter the wound. It is thus necessary to appropriately filter the ventilation air supplied to the wound.

The ventilation of the wound cavity is particularly problematic when the wounds to be treated are internal wounds or when the wound must be closed airtight via a wound dressing.

A portable wound treatment apparatus is described in EP 0 865 304 B1 for aspirating secretions out of a superficial wound covered with an air-tight surgical wound covering in which a suction pipe provided with additional lumen is connected to the surgical wound covering. The additional lumen allow air to be supplied to the suction point. The suction apparatus must be specially configured to control the air supply through the ventilation lumen.

In order to aspirate secretions out of body cavities, DE 43 06 478 A1 describes, in addition to the drainage tube leading to the suction apparatus, providing an additional tube through which preferably air is conducted to the suction point. The suction apparatus must also be equipped with corresponding measurement, control, and filtering instruments to control this air supply. Using a conventional medical suction apparatus equipped only with a suction inlet is not possible with this drainage device.

WO 2009/071933 A2 describes a negative pressure wound therapy which also uses a wound dressing to seal the wound. A sealed suction tube, which is connectable to a vacuum source and which is equipped with a perforated drain, is thereby introduced through the wound dressing into the wound cavity. In order to allow for a ventilation of the wound cavity near the suction point, an additional ventilation tube must be introduced through the wound dressing in a sealed manner. A bacterial filter is disposed at the end of the ventilation tube in a separate housing equipped with an air inlet opening. This bacterial filter is set to a fixed permeability which determines the intensity of the ventilation. In order to make ventilation possible when the given size of the pores of the bacterial filter is 0.2 µm, the bacterial filter must be designed as a relatively large-scale membrane filter. The scope of application of this solution is very limited due to the required separate filter housing and separate ventilation tube. Positioning and sealing two separate tubes results in an increased effort, specifically when caring for internal wounds that are not closed by a wound covering. Another disadvantage is that with a ventilation tube closed by a tube clamp, humidity can enter the bacterial filter through the air inlet opening of the filter housing so that the filter will become permanently inoperative due to its hydrophobic properties. This is particularly disadvantageous for mobile applications and applications where the drainage tube remains in the wound while using sanitary facilities.

DE 10 2011 052 735 A1 describes a multi-lumen medical drainage tube in which the suction lumen flows into an axial ventilation opening at its proximal end.

U.S. Pat. No. 4,735,606 describes a medical drainage apparatus in which the distal end of a multi-lumen drainage tube is placed into a body cavity, whereas the proximal end of the drainage tube is connected to a negative pressure source via collection receptacles. This drainage apparatus is connectable to a conventional negative pressure source having only one suction inlet. The problem with this solution is that a regulatable ventilation and filter unit must first be connected to the proximally open ventilation lumen so that it is sealed by a frictional connection. If this ventilation and filter unit is not or is not correctly connected, germs from the surrounding air may get into the wound to be treated. Although this medical drainage device is also connectable to conventional suction apparatuses equipped with only one suction inlet, it is not satisfactory with regard to handling, constructional design, and safety due to the type of ventilation used. The necessity of controlling the intensity of the ventilation by means of an adjustable valve in accordance with the situation across the described wide control range makes it necessary for the filter used to have a permeability, and thus a pore size, that does not meet current requirements imposed on bacterial filters.

DE 31 27 249 A1 describes a surgical drainage device with an adapter from a one-lumen to a three-lumen tube with an axial ventilation opening. Sterility cannot be provided due to the required assembly prior to use.

DE 43 06 478 A1 describes a drainage device in which a suction tube having a plurality of lumen on the patient side gives way to two separate tube sections at its proximal end, wherein a bacterial filter is embedded in the separate tube section of the additional tube.

The known technical solutions are not satisfactory with regard to compactness and handling. These solutions are in particular not adapted for use in soft tissue drainages in which the proximal end of a single suction tube is pulled with a needle through the tissue layers next to the opening of the wound from the inside to the outside.

In an embodiment, the present invention provides a medical drainage tube for treatment of wounds using a negative pressure generated by a medical suction apparatus which includes a suction tube, a suction connector, and a ventilation sleeve. The suction tube comprises at least one suction lumen, and at least one ventilation lumen comprising a ventilation lumen outer wall and a radial ventilation opening. The suction connector is arranged at a proximal end of the suction tube spaced apart from the radial ventilation opening. The ventilation sleeve is arranged at the radial ventilation opening so as to coaxially surround the suction tube. The ventilation sleeve comprises a ventilation sleeve wall comprising a ventilation sleeve inner wall arranged towards the suction tube, an annular groove arranged in the ventilation sleeve inner wall, a filter compartment arranged in the ventilation sleeve wall, a bacterial filter undetachably arranged in the filter compartment, and an air inlet opening arranged in the filter compartment. The annular groove is configured to communicate with the radial ventilation opening. The bacterial filter is configured to communicate with the annular groove. The air inlet opening is configured to connect the bacterial filter with the atmosphere. A part of the at least one ventilation lumen between the annular groove and the proximal end of the suction tube is sealed off.

SUMMARY

An aspect of the present invention is to provide a solution for a compact, very simply designed medical drainage tube with an integrated ventilation lumen to suck secretions from wounds or body cavities with which the intrusion of germs from the surrounding air through the ventilation lumen can reliably be prevented. The suction device must thereby be connectable to conventional medical suction apparatuses equipped with only one suction inlet. The drainage tube according to the present invention must also be usable for soft tissue drainages in which the proximal end of the multi-lumen suction tube is pulled with a needle through the respective tissue layers next to the opening of the wound from the inside to the outside.

BRIEF DESCRIPTION OF THE DRAWINGS

The present invention is described in greater detail below on the basis of embodiments and of the drawings in which:

FIG. 1 shows a longitudinal section of a drainage tube;
FIG. 2 shows the section A-A through the distal end of a drainage tube.

DETAILED DESCRIPTION

Figure 3:
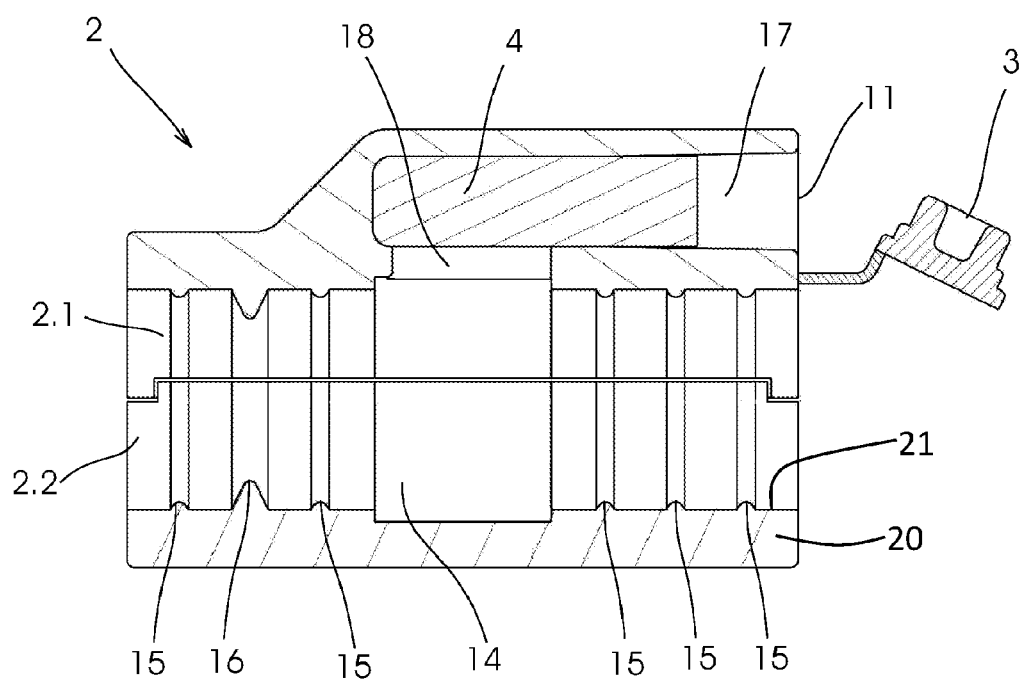
FIG. 3 shows the axial section through a ventilation sleeve without the section tube.
Figure 4:
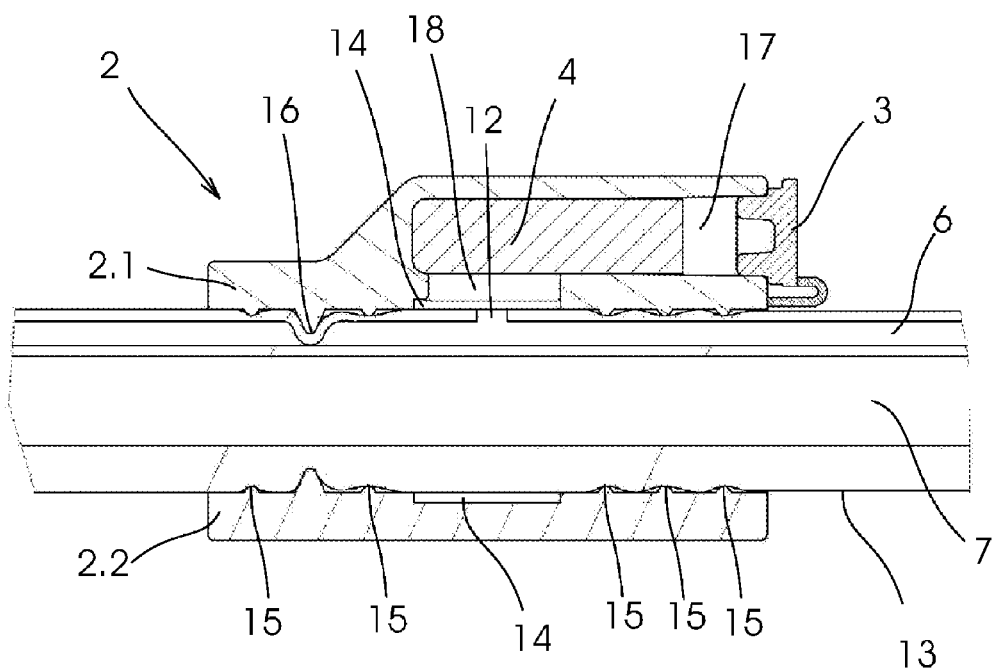
FIG. 4 shows an axial section through the detail X shown in FIG. 1.

In an embodiment, the present invention provides a continuous one-piece drainage tube with at least one suction lumen and at least one ventilation lumen, wherein the distal end of the suction lumen is designed with a perforated circumference, and the proximal end of the suction lumen is connectable to a negative pressure source. A radial ventilation opening leads from the ventilation lumen outwards, at a clear distance from the proximal orifice, and communicates with a bacterial filter undetachably disposed in a ventilation sleeve coaxially surrounding the suction tube. The permeability of the filter is adjusted to the negative pressure sources of conventional medical suction apparatuses so that when the proximal orifice of the ventilation lumen is open, a defined pressure differential is provided between the suction lumen and the ventilation lumen.

The present invention is advantageous in that the air inlet opening in the ventilation sleeve leading to the bacterial filter is oriented toward the distal end of the drainage tube. In conjunction with the arrangement of the ventilation sleeve at a clear distance from the proximal end of the suction tube, the air inlet opening leading to the bacterial filter thus is not close to the suction connector of the drainage tube. No moisture can therefore enter the bacterial filter when handling the suction connector of the drainage tube even when the stopper is not inserted in the ventilation sleeve.

In the proximal direction, the ventilation sleeve has a slant ahead of the bacterial filter which facilitates the passage through the respective tissue layers.

The construction of the ventilation sleeve, which consists of two half-shells to be connected, together with a clamping bead and a squeezing bead, allows for a cost-effective production of the ventilation sleeve and its simple attachment to the suction tube.

If a ventilation of the treatment site via the ventilation lumen is not desired, the air inlet opening leading to the bacterial filter is tightly closed by a stopper.

Another advantage of the present invention is that the intrusion of germs through the ventilation lumen is at all times prevented because of the undetachably integrated arrangement of the bacterial filter in the air passage of the ventilation lumen. By adjusting the permeability of the bacterial filter to the negative pressure sources of conventional medical wound suction apparatuses, additional means for adjusting the optimal pressure difference between the suction lumen/wound and the ventilation lumen can be dispensed with. The solution according to the present invention for connecting and disconnecting the ventilation lumen and adjusting the pressure difference allows for a very compact design of the drainage tube which does not require many accessories. This is advantageous when using portable medical wound suction apparatuses.

The use of a pipette filter with a pore size of 3 to 12 μm allows for an advantageous and space-saving arrangement in the connection unit. Connecting and disconnecting the suction lumen by way of an undetachable stopper disposed on the ventilation sleeve, which closes the air inlet opening in the ventilation sleeve ahead of the bacterial filter, is advantageous. Moisture is thereby prevented from entering the bacterial filter during uses in which the drainage tube remains in the wound, for example, when the patient uses sanitary facilities.

The suction device according to the present invention is usable for negative pressure wound therapies with or without secretion discharge.

An exemplary embodiment of the present invention will be explained below under reference to the drawings.

In the exemplary embodiment according to FIGS. 1 to 4, the drainage tube 1 according to the present invention has a one-piece, flexible, double-lumen suction tube 13. The suction tube 13 consists of the suction lumen 7 and the ventilation lumen 6. The suction lumen 7 has a perforation 8 at the distal end of the suction tube 13. The ventilation lumen 6 ends without a perforation at the distal end of the suction tube 13. The X-ray contrast strip 9 runs in the wall of the suction tube 13 (FIG. 2).

At the proximal end of the suction tube 13, the suction lumen 7 flows into the suction connector 10, whereas the ventilation lumen 6 advantageously ends at a flange-like surface of the suction connector 10.

The ventilation lumen outer wall 19 of the ventilation lumen 6 has a radial ventilation opening 12 at a clear distance from the suction connector 10. A ventilation sleeve 2, which consists of welded or glued half-shells 2.1 and 2.2, is disposed there so that it coaxially surrounds the suction tube 13 (FIG. 3).

The bacterial filter 4 is disposed in a filter compartment 17 in the wall of the half-shell 2.1. In the area of the ventilation opening 12, an annular groove 14 is formed in the inner wall of the ventilation sleeve 2, i.e., in the half-shells 2.1 and 2.2, into which the ventilation opening 12 flows. The annular groove 14 is connected outwards to the filter compartment 17 by way of an aperture 18. An air inlet opening 11 disposed in the distal direction is closable by means of a stopper 3.

On both sides of the annular space 14, a clamping bead 15, which fastens the ventilation sleeve 2 so that it tightly surrounds the suction tube 13, is circumferentially formed on the ventilation sleeve inner wall 20 of the ventilation sleeve 2. A squeezing bead 16 is circumferentially formed on the ventilation sleeve inner wall 20 of the ventilation sleeve 2 next to the ventilation opening 12 in the proximal direction. The squeezing bead 16 is radially dimensioned so that it only squeezes the ventilation lumen 6 in a tightly sealed manner in that place. When the stopper 3 is removed, the ventilation lumen 6 leading to the distal end of the suction tube can thus be actively connected to the atmosphere so that it aspirates it via the annular groove 14, the ventilation opening 12, the annular groove 14, the aperture 18, and the bacterial filter 4.

If necessary, a tube clamp (not shown in the drawings) can be attached between the ventilation sleeve 2 and the perforated area of the double-lumen suction tube 13.

In order to generate a defined negative pressure in the area of the wound cavity 5, the suction tube 13 is placed into the wound cavity 5 at least with its perforated distal end. To this end, the perforated area of the suction tube 13 may be shortened in accordance with the situation. The suction tube 13 is sealed relative to the tissue closing the wound cavity 5 or relative to a wound cover along its unperforated circumference. These sealings need to be implemented in only one location due to the double-lumen configuration of the suction tube 13.

In order to apply the negative pressure to the wound cavity 5, a medical wound suction device (not shown in the drawings) is connected to the suction connector 10. During operation of the wound suction device, the secretions accumulating in the wound cavity 5 are aspirated through the distal opening of the suction lumen 7 and its perforation 8 and transported into the receptacle of the medical wound suction apparatus (not shown in the drawings). In order to maintain the secretion flow when the wound cavity is sealed off, the air inlet opening 11 is not closed by the stopper 3. The air flowing from the air inlet opening 11 to the distal opening of the ventilation lumen 6 optimally ventilates the suction area. The airflow capacity is set to a fixed value and adjusted to the respectively used medical wound suction apparatuses. This fixed setting of the airflow is implemented by the respectively used bacterial filter 4. The bacterial filter 4 can, for example, have a pore size of 3 to 12 μm therefor. Based on the permeability resulting from this pore size, the bacterial filter 4 can advantageously be realized as a pipette filter with a length of approximately 3 to 6 mm and a diameter of approximately 2.5 mm. These geometrical dimensions advantageously make it possible to undetachably integrate the bacterial filter 4 into the ventilation sleeve wall 21. This is a prerequisite for a design of the drainage tube 1 according to the present invention that is both compact and does not require many accessories.

If a ventilation of the suction area is to be dispensed with, for example, in the case of superficial wounds or when using wound coverings made of gauze, sponges or semi-permeable films, the air inlet opening 11 is tightly closed with the stopper 3 formed on the ventilation sleeve 2, thus interrupting the air flow in the ventilation lumen 6. In this state, moisture cannot penetrate into the hydrophobic bacterial filter 4 and cause permanent damage. When the stopper 3 is inserted, the patient can expose himself/herself, with the inserted drainage tube 1, to increased moisture in a sanitary facility.

The X-ray contrast strip 9 running in the wall of the suction tube 13 serves to make it visible on X-ray photographs.

The configuration of the suction connector 10 as a 4 mm standard connector provides the adaptability of the drainage tube 1 according to the present invention to all current medical suction systems.

The present invention is not limited to embodiments described herein; reference should be had to the appended claims.

LIST OF REFERENCE NUMBERS 1 drainage tube
2 ventilation sleeve
2.1 half-shall
2.2 half-shell
3 stopper
4 bacterial filter
5 wound cavity
6 ventilation lumen
7 suction lumen
8 perforation
9 X-ray contrast strip
10 suction connector
11 air inlet opening
12 ventilation opening
13 suction tube
14 annular groove
15 clamping bead
16 squeezing bead
17 filter compartment
18 aperture
19 ventilation lumen outer wall
20 ventilation sleeve inner wall
21 ventilation sleeve wall

What is claimed is:

1. A medical drainage tube for treatment of wounds using a negative pressure generated by a medical suction apparatus, the medical drainage tube comprising:
   a suction tube comprising,
      at least one suction lumen, and
      at least one ventilation lumen comprising a ventilation lumen outer wall and a radial ventilation opening;
   a suction connector arranged at a proximal end of the suction tube spaced apart from the radial ventilation opening; and
   a ventilation sleeve arranged at the radial ventilation opening so as to coaxially surround the suction tube, the ventilation sleeve comprising, a ventilation sleeve wall comprising a ventilation sleeve inner wall arranged towards the suction tube, an annular groove arranged in the ventilation sleeve inner wall, the annular groove being configured to communicate with the radial ventilation opening, a filter compartment arranged in the ventilation sleeve wall, a bacterial filter undetachably arranged in the filter compartment, the bacterial filter being configured to communicate with the annular groove, and an air inlet opening arranged in the filter compartment, the air inlet opening being configured to connect the bacterial filter with the atmosphere, wherein, a part of the at least one ventilation lumen between the annular groove and the proximal end of the suction tube is sealed off.

2. The medical drainage tube as recited in claim 1, wherein, the ventilation sleeve further comprises clamping beads circumferentially formed on the ventilation sleeve inner wall and arranged on both axial sides of the annular groove, and the ventilation sleeve is provided as a first assembled half-shell and a second assembled half shell.

3. The medical drainage tube as recited in claim 1, wherein the ventilation sleeve further comprises a squeezing bead circumferentially arranged next to the radial ventilation opening in the proximal direction, the squeezing bead being configured to seal off the at least one ventilation lumen.

4. The medical drainage tube as recited in claim 1, further comprising:

a stopper, wherein, the air inlet opening is oriented toward a distal end of the drainage tube and is configured to be closed by the stopper.

* * * * *